United States Patent
Madarasz et al.

(10) Patent No.: US 6,591,121 B1
(45) Date of Patent: Jul. 8, 2003

(54) MEASUREMENT, DATA ACQUISITION, AND SIGNAL PROCESSING

(75) Inventors: Frank L. Madarasz, Madison, AL (US); Darell Engelhaupt, Madison, AL (US); Ramarao Inguva, Huntsville, AL (US); David P. Krivoshik, East Amwell, NJ (US); R. Joseph Milelli, Simi Valley, CA (US); James K. Wyly, Bow, NH (US)

(73) Assignee: Xoetronics LLC, Ringoes, NJ (US)

( * ) Notice: Subject to any disclaimer, the term of this patent is extended or adjusted under 35 U.S.C. 154(b) by 0 days.

(21) Appl. No.: 09/502,248

(22) Filed: Feb. 17, 2000

Related U.S. Application Data

(63) Continuation-in-part of application No. 09/249,677, filed on Feb. 12, 1999, now Pat. No. 6,236,870, which is a continuation of application No. 08/858,260, filed on May 19, 1997, now Pat. No. 5,871,442.
(60) Provisional application No. 60/024,727, filed on Sep. 10, 1996.

(51) Int. Cl.[7] .................................................. A61B 5/00
(52) U.S. Cl. ........................ 600/310; 356/364; 600/316
(58) Field of Search ................................. 600/310, 316, 600/318, 319; 356/364, 366, 367

(56) References Cited

U.S. PATENT DOCUMENTS 5,956,144 A * 9/1999 Kaplan et al. ............... 600/310
6,236,870 B1 * 5/2001 Madarasz et al. ........... 600/310

* cited by examiner

*Primary Examiner*—Eric F. Winakur
(74) *Attorney, Agent, or Firm*—David P. Krivoshik; Mathews, Collins, Shepherd & McKay

(57) ABSTRACT

In an opto-electronic device utilizing a band of light for quantitative analysis of a specimen containing a target molecule, the opto-electronic device comprising a specimen cell adapted for receiving the specimen and for transporting the band of light, a device for comparing the band of light before entering the specimen with the band of light after exiting the specimen, wherein the target molecule. The device for comparing comprises: an optical sensor; and, a signal processor for determining a quantitative level of the target molecule within the specimen. The signal processor utilizes Bayes' Theorem for determining the quantitative level of the target molecule within the specimen.

6 Claims, 3 Drawing Sheets

MEASUREMENT, DATA ACQUISITION, AND SIGNAL PROCESSING

CROSS REFERENCES TO RELATED APPLICATIONS

This application is a continuation-in-part of U.S. patent application Ser. No. 09/249,677 filed on Feb. 12, 1999, now issued U.S. Pat. No. 6,236,870, which is a continuation of U.S. patent application Ser. No. 08/858,260 filed on May 19, 1997, now issued U.S. Pat. No. 5,871,442, which claims the benefit of U.S. Provisional Patent Application Serial No. 60/024,727, filed on Sep. 10, 1996.

BACKGROUND OF THE INVENTION

In any experimental situation, decisions concerning the idea of measurement need to be made continually. This may at first seem trivially simple. But the science of metrology, and the very act of the measurement process, are both fascinating and complex. The two large questions are: 1. what we wish to measure and, 2. how to do it. Each question is far from simple.

What actually is desired to be measure is crucial, for answering this question assumes an accurate working knowledge of what is happening in the experimental set up, the basic mechanisms of nature with which we are dealing, and the well defined features of those natural processes which are of interest. These features may be such things as temperature, light intensity, angular displacement, the velocity of something, etc.

How to do this is the next question. Very often things are not measured directly, but indirectly by measuring something else than the intended result. It is vital to be certain that this something else always represents the final desired quantity. For example, with a radar gun used to measure speed of a moving vehicle, the dopler frequency shift in a microwave beam is the indirect quantity measured. However an airplane speed check of a moving vehicle, made with road markers and a stopwatch, measures speed directly.

So in addition to the primary variable, the thing to be determined, there are often one or more dependent or intermediate variables, which are the quantities actually measured. Through electronic circuitry the radar gun reformulates the frequency change into an electronic impulse, which powers the display which can be read.

In addition there is the question of a particular transducer, or sensor: the device which translates one form of information into another (usually more convenient) form. An oral fever thermometer transforms sub lingual temperature into a distance scale via liquid in a tube.

Once the desired information is acquired, and stored in some manner, it is often very useful to transform the data yet again in some say. The transformation of the data, and the reasons for performing it, are usually described by somewhat sophisticated mathematics. Despite this data transformation, what happens may be viewed as an extension of the thermometer taking temperature into distance, or the way a conical measuring cup translates volume into distance in a non-linear way—being more sensitive at smaller measurement volumes. This last example anticipates the enormous field of the processing of data, especially its valid statistical treatment (in order to maximize useful information without being misled), and the field of data transformation (to allow occult information to become self-revealing).

SUMMARY OF THE INVENTION

In accordance with the present invention, there is provided in an opto-electronic device utilizing a band of light for quantitative analysis of a specimen containing a target molecule, the opto-electronic device comprising a specimen cell adapted for receiving the specimen and for transporting the band of light, a device for comparing the band of light before entering the specimen with the band of light after exiting the specimen, wherein the target molecule. The device for comparing comprises: an optical sensor; and, a signal processor for determining a quantitative level of the target molecule within the specimen. The signal processor utilizes Bayes' Theorem for determining the quantitative level of the target molecule within the specimen.

BRIEF DESCRIPTION OF THE DRAWINGS

A more complete understanding of the present invention may be obtained from consideration of the following description in conjunction with the drawings in which.

DETAILED DESCRIPTION OF VARIOUS ILLUSTRATIVE EMBODIMENTS

Figure 1:
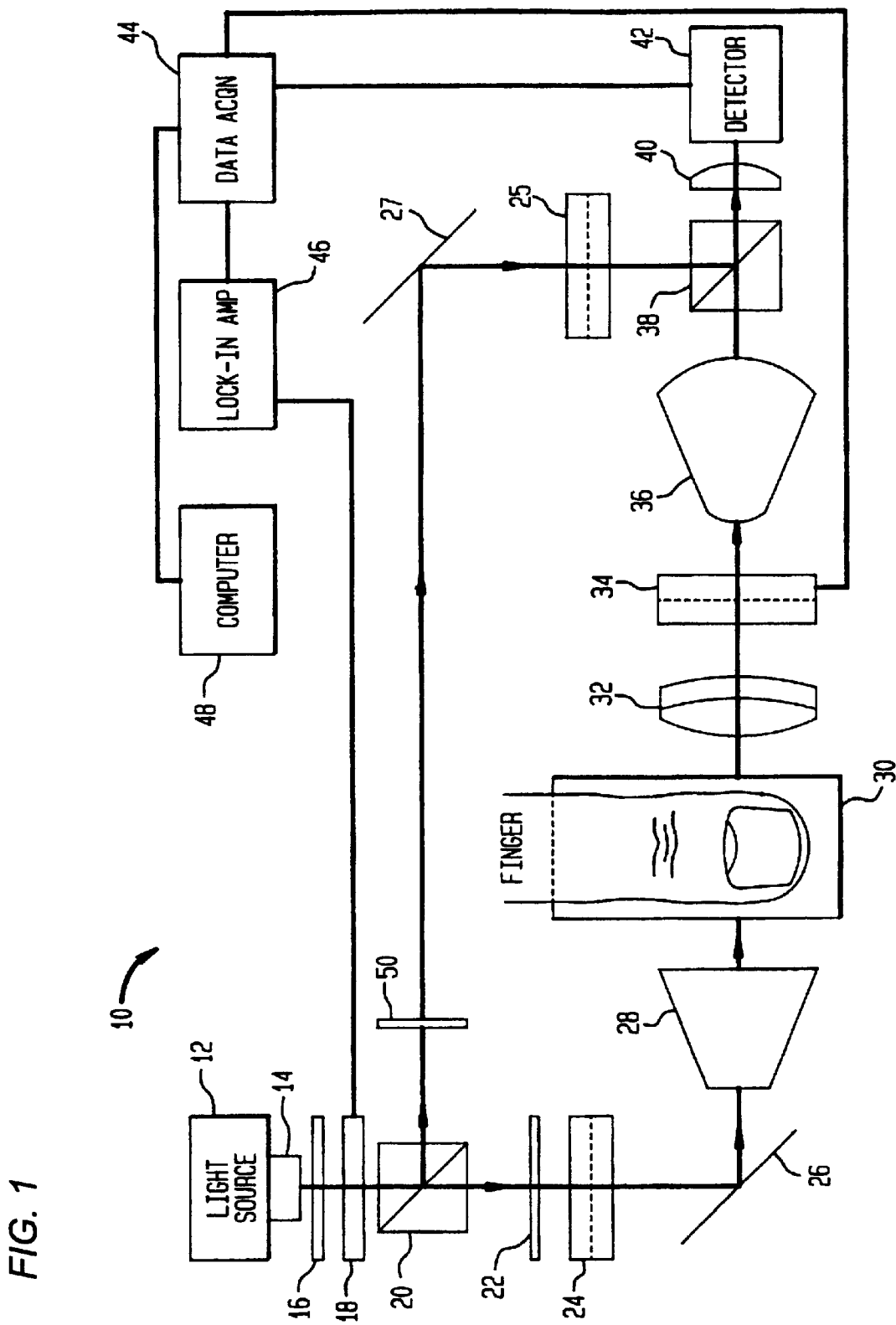
FIG. 1 is a block diagram of a first illustrative embodiment of the Photonic Molecular Probe.

Although the present invention is particularly well suited for use with the Photonic Molecular Probe, and shall be described with herein, it is equally well suited in a variety of other areas requiring similar data analysis, including but not limited to other optical applications requiring comparison of optical signals for quantitative determination of a target molecule.

While the Photonic Molecular Probe is non-invasive and employs NIR light, it DOES NOT rely on linear absorption. The Photonic Molecular Probe uniquely exploits the chiral asymmetry, geometrical, properties of the target molecule, glucose in this case, which influences the light in a process called Circular Dirchroism (CD), chiral absorption. The result is a much richer source of information leading to the unambiguous structural identification of the target molecule. Concurrent with CD is another chiral process called Optical Rotary Power (OR). Any molecule or substance, which exhibits CD and OR, is said to be Optically Active.

Optical activity has its origins imbedded in the $19^{th}$ century. As early as 1811 Jean Baptist Biot discovered OR (sometimes ORD, D is for dispersion indicating it is a frequency dependent phenomenon) in turpentine. Others who significantly contributed to the field were Arago, Fresnel, Herschel, Pasteur, Le Bel, van't Hoff and Boltzmann. In 1864 Faraday discovered magneto-optical activity. The term chiral was introduced by Lord Kelvin in 1884 in his Baltimore lectures. It was Andre Cotton who in 1896 discovered CD. Collectively, ORD and CD are known as the Cotton Effect. Both are frequency or wavelength dependent mechanisms. This dependence is a strong function of the asymmetrical structure of the target molecule.

In the $20^{th}$ century, great fundamental theoretical advancements in the underlying physics were made including the quantum mechanical descriptions of these phenomena. Only recently, with the explosion of electronic and optical high technologies, have scientists been able to exploit the richness of ORD and CD. In general, organic molecules, such as glucose, are structured in a spiraled form: i.e., they have a definite helicity or handedness, just as a screw can be right or left handed. It is this helicity which gives a molecule its ability to rotate the polarization of the incident light. For example, dextrose (d-glucose) is by convention right-handed since, when viewed from the perspective of light emerging from the sample, the polarization axis rotates in a clockwise direction. On the other hand, levulose (fruit sugar) is left-handed since it rotates the polarization axis in a counterclockwise direction. Molecules or material, which exhibit this kind of optical activity are said to possess Optical Rotary Power. In particular, depending upon the action on the polarization of the incident light, these are termed dextrorotary or levorotatory, respectively.

The magnitude of the angle through which the polarization direction rotates is proportional to the square of the frequency of the incident light. It also is a strong function of the type of material or molecular structure being irradiated. This functional dependence on the physical properties of the medium classically manifests itself in the difference of the indices of refraction for right- and left-handed polarized light, which make up linear, and elliptical, polarization states, producing a relative phase shift between the two. (Linear and elliptically polarized light are a result of the superposition of two circularly polarized beams of light— one rotating clockwise, the other counter-clockwise.)

If, on the other hand, there is a difference in the absorption between the right- and left-handed circularly polarized light making up the polarization state, the phenomenon of Circular Dirchroism exists. For example, if the polarization of the light irradiating the sample were purely elliptical, not only would the ellipse rotate, due to the OR, about an axis parallel to the direction of propagation of the light but also the ellipse would distort: i.e., its eccentricity would change. Both processes generally occur together. This functional dependence on the physical properties of the medium classically manifests itself in the difference of the absorption coeficients for right- and left-handed polarized light, which make up linear, and elliptical, polarization states.

The Photonic Molecular Probe (Photonic Molecular Probe) is a non-destructive/non-invasive monitoring device capable of probing and unambiguously identifying quantitatively a target molecule within a mixed specimen. It is multi-faceted in that it incorporates several physically distinct modes of operation. Because of its operational capabilities, the Photonic Molecular Probe has a myriad of potential a plications—for example: monitoring blood constituents such as alcohol, glucose, hormones and triglycerides; molecular detection in medical and biological research; food inspection; in the plastics industry—plastic waste disposal sorting and inspection/quality control; continuous monitoring of fermenting substances; and detection of chemical and biological warfare agents. The device incorporates advanced designs for the optimization of data collection and device miniaturization, state-of-the-art optical and electronic component technology as well as sophisticated data reduction techniques.

Target molecules can be any of a variety of illicit or abused drugs, licit drugs, blood chemistry profile components, hormones, white blood cell counts, red blood cell counts and morphology, as well as numerous other substances. Illicit or abused drug target molecules can include amphetamines, barbiturates, benzodiazepines, cocaine, methadone, opiates, phencyclidine, propoxyphene, secobarbital, tetrahydrocannabinol as well as numerous other illicit drugs. Target molecules for classes of toxic assays of licit drugs can include non-steroidal anti-inflammatory agents (NSAIDs), tricyclic antidepressants (TCAs), anti-psychotics, analgesics, antihistamines, anti-seizure drugs, anti-manic drugs, methanol, mahaqualone, anti-coagulants, anti-hypertensives, salicylate, strychnine, anti-asthma medications, cardiac medications, antibiotics, anti-virals as well as numerous other licit drugs. Blood chemistry profiles present many potential target molecules including albumin, alkaline phosphatase, total bilirubin, calcium, chlorine, cholesterol, creatinine, glucose, lactic acid dehydrogenase, potassium, total protein, glutamic oxaloacetic transaminase, SGOT, SGPT, sodium, triglycerides, urea nitrogen, uric acid, carbon dioxide and numerous others. Hormone tests for steroids such as at athletic competitions, human chorionic gonadotropin (HCG) for pregnancy and precancer tests, T-3, T-4, thyroid stimulating hormone (TSH) as well as other hormones can be target molecules.

Referring to FIG. 1 there is shown a block diagram of a first illustrative embodiment of the present invention Photonic Molecular Probe 10.

A light source 12, such as a tungsten filament lamp, is used within an envelope with an internal reflector behind the envelope, similar to a sealed beam head lamp. The envelope contains a halogen gas, usually a mixture of an inert gas such as xenon, and a fluoride or chloride bearing gas. The filament of the light source 12 is typically heated to approximately 2900K and emits, by blackbody emission, in the range 320–2500 nm. For wavelengths longer than about 2500 nm a silicon carbide globar lamp at 1500K is used.

The halogen gas mixture is ionized at the high temperature by the filament, and emits short wavelength spectral lines characteristic of the ionized elements similar to a conventional mercury-inert gas fluorescent lamp. The gas also helps stabilize the temperature effects. With a specialty lamp consisting of both tungsten-halogen and florescent characteristics an advantage in calibration could be realized.

A collimating lens 14, may be a part of the lamp, which contains the light source 12, or may be optically coupled to the lamp. Lamps are available with either focusing or collimating lenses, and internal reflectors which provide a degree of elliptical as well as linear polarization (partial polarization).

A color filter wheel 16 can be used to obtain shorter bandpass frequencies for analyses simplification. The color filter wheel 16 is optically coupled to the collimating lens 14.

Choppers are used in spectrometers principally for one of two reasons: stray light control and double beam operation. In the Photonic Molecular Probe 10 a chopper 18 is optically coupled to the color filter wheel 16. The chopper 18 is electronically coupled to a Lock-in Amplifier 46.

For stray light control the location of the chopper 18 allows timing of a lock-in amplifier 46 to select data which is highly immune to extraneous light. Frequency shifts due to the position of the polarizing elements, and the polarization shift of the selected wavelength, provide quantitative data as the target molecule interacts with the light from the polychromatic source 12. This data is a complex, superimposed non-imaging spectrum, which contains information about retardation, wavelength and amplitude. The use of the chopper 18 can impede the Photonic Molecular Probe's operation by limiting the speed of data collection. However, proper enclosure designs reduce stray light, reflections, and external illumination.

A double beam operation is obtained by inserting a second sample holder between mirror 27 and polarizing element 25, and also replacing polarizing beamsplitter 20 with a reflective version of chopper 18 mounted at 45 degrees to the path between the collimating lens 14 and a half wave plate 22. This unit would be similar to a conventional chopped double-beam instrument. In addition, if desired, the double beam instrument allows for a self calibrating feature by a real-time comparison of known to unknown concentrations of the target specimen: i.e. self-calibration. While double beam operation is useful for an absorbance or transmittance device, timing options of other movable elements offer better choices for a polarization device.

A polarizing beam splitter 20 is optically coupled to the chopper 18. The operation of the Photonic Molecular Probe requires partially polarized polychromatic light to permit markers for the transform analysis. By multiple reflections of a polychromatic beam each frequency becomes partially polarized with a slightly different angular dependence resulting in the a series of markers distributed on an essentially elliptical envelope. A higher degree of polarization can now be obtained by the use of polarizing elements which are minimally affected by lamp aging. By using a broadband beam splitting polarizer a relatively unpolarized light source is split into the S and P polarization states at a 90 degrees exit angle. Additional options include the use of separate polarization devices, such as dichroic polarizers, which are selective at certain wavelengths due to the anisotropic material used.

A half wave plate 22 can be used to control the intensity of the beam to avoid saturation of the detector during calibration or measurements of more nearly transparent materials. The half wave plate 22 is optically coupled to the polarizing beam splitter 20.

A quarter wave plate 50 is used in the reference beam path to control the ellipticity of the beam and also may be used for interference alignment if coherent light is used. The quarter wave plate 50 is optically coupled to the polarizing beam splitter 20.

A polarizer element 24 is optically coupled to the half wave plate 22. The polarizer element 24 is movable and may be dichroic to permit frequency (i.e. wavelength) dependence. The polarizing element 24 is stepped once as an analyzer 34 is incrementally rotated to at least some multiple of 90 degrees. This allows the wavelength dependence of the eccentricity of the polarization ellipse of the partially polarized light through the polarizing beam splitter 20 to be utilized without bandpass filters. An alternative is to use a set of filters at the color filter wheel 16.

If a greater portion of the S polarization s ate is selected at the polarizing element 24, then the analyzer 34 can be set to transmit the P polarization state to achieve interference at a beam combiner 38.

A first flat mirror 26 is used to direct he partially polarized light to a finger cell 30 through a collimator 28 without chromatic aberration. The reflection at the first flat mirror 26 rotates the polarization 45 degrees counter clockwise while retaining the polarization markers.

A second flat mirror 27 is used to direct the optical output of the quarter wave plate 50 to a second polarizing element 25. The second polarizing element 25 is optically coupled to the beam combiner 38.

A collimator 28 minimizes extraneous scattered light and expand the beam to one of a larger cross-section and lower amplitude, which reduces heating and increases optical interaction with the finger fluids. The collimator 28 can be a reflective device to minimize chromatic effects. The chromatic shift is fixed and can be dealt with in calibration if a lens arrangement is used.

A finger cell 30 can be constructed with cylindrical lenses to optimize the beam path through the finger. While this will affect the polarization it can be used advantageously if a conjugate cylindrical lens is used on the exit side. The light into the finger is partially scattered upon exit. This in turn gives a logarithmic amplitude dependence of light transmitted with respect to cell path length through the sample. Hence by linear collimation and recollection of the scattered light, these lenses minimize problems with varying finger sizes. The intensity of light through the finger is a function of the path length and the concentration of any analyte should be consistent with the normalized intensity. The distance between the cylindrical lenses can be measured as part of calibration to a particular patient. Normalization to other standards, such as water, can also provide accurate calibration. In this case, the amount of analyte divided by the water signal will provide the normalization.

For other embodiments of the present invention the finger cell 30 is generally a specimen cell which is adapted for receiving a particular mixed specimen. While the present invention is particularly well suited for use in non-invasive analysis it is equally well suited for use in the analysis of mixed specimens which may have been collected by an invasive technique as well as specimens which originated from other sources such as a laboratory, production environment or a process operation. Mixed specimens collected by traditional invasive techniques into a vial may be placed into a suitably adapted specimen cell for analysis. Where continuous quantitative analysis is advantageous, such as in a process operation, the specimen cell may be adapted for placement within the operation and may permit the mixed specimen to flow through the specimen cell.

A condensing lens 32 is optically coupled to the finger cell 30 and collects the dispersed light without adding additional depolarization.

The analyzer 34, which is optically coupled to the condensing lens 32, is a movable non-dichroic polarizing element. It is used to track signal variations derived by light intensity versus angular position. The light in this case is partially polarized in a wavelength dependent manner by both the light source 12 and the polarizer element 24. A complete signal is obtained by incrementally moving the analyzer 34 (or electronically scanning a spatial light modulator) through at least 180 degrees. Next, the polarizing element 24 is incremented by a predetermined value, preferably small, to provide a shift in the dichroism and polarization. The analyzer 34 is again scanned at least 90 degrees, or preferably 180 degrees, and the data compared to the previous data.

The difference of data collected when the analyzer 34 is rotated the same 90 degrees (starting position the same), and the polarizing element 24 is stepped, yields phase sensitive differences due to polarization and is influenced by wavelength sensitive dichroism. Another mode of operation is to spin the analyzer element 34 and synchronize an oscilloscope to sweep each half rotation. This will provide a station try signal. Now the polarizing element is incremented to observe the difference. The data is stored digitally, in columns and rows, for further analysis employing various digital filters. In addition, interferrometric data will be produced which can be analyzed with frequency transform methods.

This process can be repeated for positions of the polarizing element 24 to 90 degrees to complete the spectrum. If an opaque beam block is placed between the second mirror 27 and the second polarizing element 25, and no finger is present, then a characteristic signal is achieved for the analyte path. Alternatively, if an opaque block is placed in the cell, then a source calibration is achieved.

A beam reducer 36 can use reflective Cassegrain optics to reduce chromatic shift. Polarization, albeit fixed, is dominant over a lens. The beam reducer is optically coupled between the analyzer 34 and the beam combiner 38.

The optical path between the collimating lens 14 and the analyzer 34 is now crossed with the path between the collimating lens 14 and the second polarizing element 25, producing an initially dark signal at the beam combiner 38, without a chiral sample with no chirality in the finger cell 30. This is because it should be easier to detect small increases in the intensity of light in a dark environment than small decreases in the intensity of light in a bright environment. Note the 45 degree rotation. Furthermore, although the source may not be completely coherent, a coherence path length does exist.

Regardless of whether phase information is collected at separated frequencies by the polarizer element 24, or by any other means, whole blood will yield a very complicated spectrum comprised of a system of superimposed spectra. The polarizer detects primarily phase information.

By using a dual path approach, instead of the partially polarized single path device, two very important goals are achieved.

First, a reference signal is always available for calibration, thereby allowing time-independent calibrations. Furthermore, independence from calibration specific to a given patient becomes a reality, especially with a finger cell 30 that is adjustable.

Second, overlapping Lorentzian absorption bands generate a complex spectrum which can be expressed as an infinite sum of sine and cosine terms. Additionally, information from intensity versus polarizing analyzer position (with sample present) is continuous, and will therefore also have phase sensitive information. One way to handle this massive amount information is to subtract successive intensity data collected throughout the rotation of the analyzer 34 at discrete steps of the polarizer element. This data is combined at the beam combiner 38 with the conjugate polarized original light (S vs. P), yielding interferometric or retardation data. This provides for a real Fourier Transform (or other frequency dependence) instrument. The analysis can be handled similarly to known FTIR spectrometer methods wherein the spectrum is calculated from the interfrogram comprised of intensity information from the spectrum of the source minus that of the simple. Since the light is not monochromatic the interferogram is now no longer a simple cosine function.

A forward difference approach may be used to remove large spectral changes and allow observation of the smaller spikes. The application of wavelet theory can be very useful, however the complexity of this task can be reduced by subtraction of intensity data collected at different increments of the polarizer element 24 while rotating the analyzer 34. This then permits true wavelength dependence to be observed and retarder for frequency analysis.

If the polarizing analyzer is rapidly rotated in a continuous fashion, the retardation intensity at the output of a detector 42 versus the position of the polarizing element 24 is a shifting spectrum. The sample information is then derived from successive subtractions of intensity throughout the rotation of the analyzer 34, in any multiple of 180 degrees, plotted against the angular position of the polarizing element 24. As mentioned previously, direct viewing with an oscilloscope is possible by synchronizing in rotation multiples of 180 degrees for each sweep of the oscilloscope.

If the pixel size of the detector 42 is less than the beam diameter from the beam combiner 38 then a condensing lens 40, or focusing lens, can be used by optically coupling the condensing lens 40 between the detector 42 and the beam combiner 38.

The detector 42 can be a single element high speed photo detector diode or photocell having an array of detectors with separate wave length response. A data acquisition system 44 is electrically coupled to the detector 42 and the analyzer 34. An analysis computer 48 is electrically coupled to the data acquisition system 44. For high resolution accuracy a lock-in amplifier 46 is electrically coupled to the chopper 18 and the data acquisition system 44.

Figure 2:
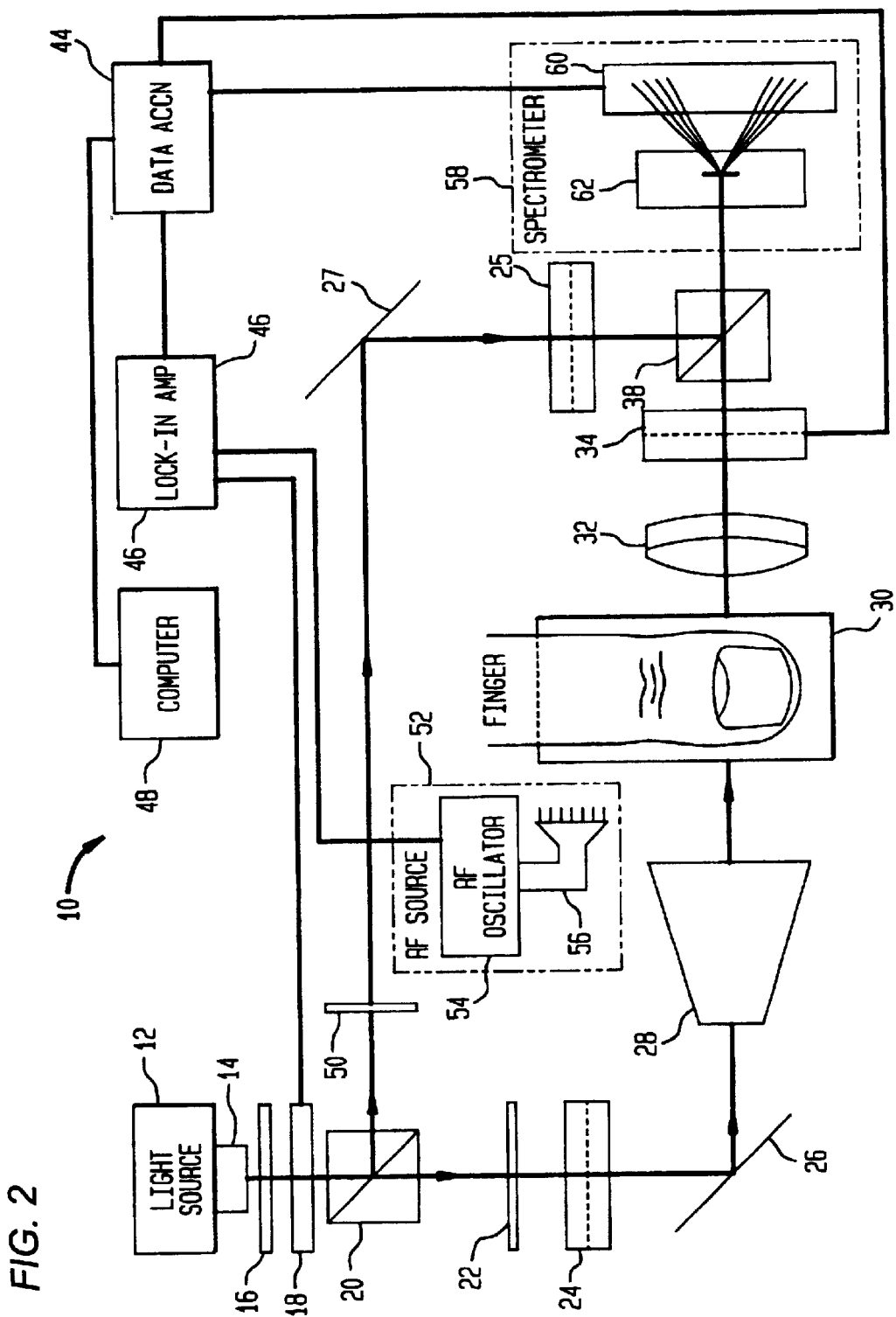
FIG. 2 is a block diagram of a second illustrative embodiment of the Photonic Molecular Probe; and, FIG. 3 is a flow chart of data acquisition and analysis.

A more versatile instrument is possible by using a small monolithic spectrometer and an array diode to obtain color (or spectral) information similar to FTIR instruments. Referring to FIG. 2, a second illustrative embodiment of the present invention Photonic Molecular Probe which is specifically designed to make possible the assay of substances with no naturally occurring inherent chirality is shown. In this way a snapshot of the spectrum is obtained each time an event signal is triggered. Elements that have similar functions as those is FIG. 1 have been assigned the same reference number and are not again described in detail. For example, each time the polarizing element 24 is incremented, such as when the analyzer is at zero and 180 degrees, a spectrum can be saved. These spectra can then be added for small ranges of the polarizing element 34 known to be specifically active for a particular analyte. Since the spectrum is direct and obtained by a detector array 60 it is not necessary to decompose the retardance data to obtain sample information. An RF source 52 causes directional alignment of certain achiral molecules to assist in detection and identification.

The RF source 52 is electrically coupled to the lock-in amplifier 46 and coupled to the specimen in the finger cell 30. RF source 52 is comprised of an RF oscillator 54 and a resonant coupler 56, such as a coil or dichroic antenna, to excite the molecules during measurement. The output of the beam combiner 38 is optically coupled to a spectrometer 58. The spectrometer 58 is comprised of the detector array 60 and a beam separation element 62, such as a monochrometer. The spectrometer 58 is electrically coupled to the data acquisition system 44.

Additionally, since noise is random, the noise is reduced by the square root of n samples taken and added over the limits of collection and computation. If for example, in the first embodiment of the Photonic Molecular Probe, 3600 data points are collected in the 360 degrees rotation of the analyzer 34, and polarizer element 24 is incremented one degree for each revolution of the analyzer, for 360 degrees, then about 1.3 million data points are rapidly achieved at nominal collection rates. This data can be plotted as the transform of the difference in any two rows of intensity versus position of the analyzer for two corresponding positions of the polarizer element 24. This can alternatively be performed with the second mirror 27 turned or blocked so as to produce a single pass instrument.

With this approach much more versatility is possible from the double pass than from a single pass device. Consider observing retardation data with the second mirror 27 in place. Assume 3600 data points are observed with a Fast Fourier Transform (FFT) taken of the difference of successive rows as the polarizer element 24 increments. For 360 values of the polarizer element 24 then 1.3 million values of retardation are decomposed to a transform spectrum, noting that this spectrum is not a discrete wavelength spectrum but an interferogram source spectrum none the less. A presentation of intensity transform vs. position of the analyzer 34 and the polarizer element 24 is a 3-D graphical representation of the chiral (and other absorption) interference due to the molecular activity in the finger cell 30. In order to excite polar molecules and molecules of low chiral activity (e.g. some substances other than glucose), it is possible to add the RF source 52. For analysis of very light elements direct current electrophoresis and/or a large magnetic field may also be required, utilizing NMR procedures.

Most FFT procedures use $2^n$ data sets where the abscissa (or rotational position in this case) may be generated once rather than measured. In other words, the angular position is repeated and so it becomes necessary only to court the output control steps rather than measure the actual position of the rotating device. Therefore an analog signal marked by steps of the polarizing element 24 can be stored digitally and, if the rotation is fairly smooth, very good values for angular position could be substituted. With this process values of rotational position not related to direct measurements can be generated: i.e. 4096 data points per revolution ($2^{12}$) for instantaneous response could be synthesized in real time. If it is not possible to achieve the needed rotational correlation exactly enough each time then a high resolution index device is used determine the position of the analyzer 34 and the data acquisition system 44, and the analysis computer 48 becomes the limiting factor of the speed of operation. The lock-in amplifier 46 may be omitted in a portable or lower cost version, however this will be at the cost of some accuracy. Since the data collection at the analyzer 34 is very position (and environment) dependent, the lock-in amplifier 46 needs to synchronize the light blocking function of the chopper 18 and the data acquisition system 44 at rather high speed, especially in a research or laboratory version of the present invention Photonic Molecular Probe where maximum performance is required. Spatial light modulator active optical devices exist which may be substituted for the chopper 18 or the analyzer 34 but presently remain expensive although experimental versions are available.

Other data reduction procedures can be utilized, such as wavelet theory or boxcar methods, which will correlate the small difference signals ideally. Other methods of analyzing blocks of data for optical spectrometers and other instruments are well known to those skilled in the art.

Data Processing Requirements

The specific data processing requirements for the Photonic Molecular Probe will depend upon the sophistication of the device model, which can be highly tailored to the specific needs at hand. A significantly degraded (i.e. simplified) version of what is to follow may be sufficient for most applications.

The data collection system in its most general form may be envisioned as consisting of a two dimensional sensor array coupled to the sensors for the angular positions for one or two optical elements in the instrument, all synchronized to the data processing clock either directly or indirectly through another intermediate clock. The sensor array may be frequency (i.e. color) sensitive, and this may prove to provide additional substance characterization information, and possibly further reduce the sophistication needed in the data acquisition of the other parameters mentioned above. Simplifications in this most general detection system may include collapsing the array to a line or a point, needing only one instead of two positionable optical elements, in addition to others.

While the data processing is done completely on board the Photonic Molecular Probe, the capability of interfacing with external computers exists. The sensed signal is represented by a two dimensional intensity array which, when combined with the information from the polarizing analyzer, contains the crucial angular information previously discussed at length. This signal is highly noise immune. One important observation about this configuration is that the techniques of wavelet transforms and Hadamard transforms may be of great use. This results in a significant reduction in the required computational power, and therefore enhanced possibilities for miniaturization, and portability, and substantially reduced costs. One example of this is in dealing with the two dimensional optical display, in which case the anti resolution, orthogonal, and biorthogonal wavelet transforms can prove quite useful.

Essentially wavelet expansions are just another form of convenient expansions, not unlike Fourier or Hartley transforms, of members of a function space. One unique characteristic is that wavelet transforms map scalar variables into a two dimensional complex domain, and it is this characteristic from which much of their usefulness derives.

The specific wavelet construct to be used in the signal processing will depend on the target molecule and the data acquisition. A general approach to the Photonic Molecular Probe signal processing/discrimination is based on a well known conditional probabilistic reduction method known as Bayes' Rule. The uniqueness of employing the Bayesian method with the Photonic Molecular Probe lies in the fact that very precise physical models can be built directly into the method. For example, atomic form factors which characterize the electronic structure of various target molecules, can be used for cellular image enhancement. Structure factors (analogues to those used in x-ray diffraction) are another example which characterize the signature of various concentrations of target molecules in solution. The physical models can be all empirical, all theoretical, or a combination of both.

In general then, the expression for the data vector D is given by $$D(\theta)=F(\theta, u)+N(\theta),\qquad \text{Equation 1.}$$

where $D(\theta)$ is a function of sampling variable(s) such as polarimeter angle $\theta$, or time t, and $N(\theta)$ is the noise which is assumed to be additive. As with the physical model function, the noise can be represented empirically, theoretically (Gaussian for example), or a combination of both. The physical model function F is then expanded in a set of basis functions $G_j$ containing a set of parameters, such as the concentration of the target molecules in solution, frequencies, decay rates, chirp rates (or any other quantities which may be encountered in the measurement process), collectively denoted by the vector u:

$$F(\theta, V)=\Sigma B_j G_j(\theta, u),\qquad \text{Equation 2.}$$

where $V=V(B; u)$. The physical model functions are the atomic form/structure factors, and the basis functions are the appropriately constructed wavelets. The $B_j$ are the associated expansion coefficients.

In the time series problem for example, F would represent the set of functions that would accurately model the time response of the system to an input pulse used as a probe. u could represent frequencies and decay rates characteristic of the system under study. Of interest is the probability of a given value for u which is conditioned on the data D and any prior information, I. This probability, denoted by $P(u|DI)$, is obtained through the use of Bayes' Rule:

$$P(u|DI) = P(D|uI)P(u|I)/P(D|I),\qquad \text{Equation 3.}$$

where $P(u|I)$=prior probability density for u, which summarizes all the prior knowledge on u, and $P(D|uI)$= likelihood function. An estimate of u can be obtained either by maximizing $P(u|DI)$ with respect to u, or by calculating its first moment:

$$<u> = \int u\, P(u|DI)du. \qquad \text{Equation 4.}$$

The second moment, $$<uu> = \int uu\, P(u|DI)du, \qquad \text{Equation 5.}$$

gives the correlation on the estimate of u.

The Photonic Molecular Probe is capable of operating in a wide spectral region including Long Wavelength to Short Wavelength Infrared, Visible and Utra-Violet regions by using an elliptical/partially polarized polychromatic (sometimes referred to as chromatic polarization) radiation source with a variety of opto-electronic processes, all of which fundamentally correspond to basic scattering processes, to identify the signature and concentration of various target molecules within a mixed specimen, with a minimum of software for data reduction, yielding a highly accurate, cost effective analysis.

The basis of the Photonic Molecular Probe is in its use of circular dichroism and optical rotatory power or dispersion which together are known as the Cotton Effect, over an appropriate frequency range determined by the target molecule specie. These processes are a manifestation of the molecule's chirality—its handedness. In general, organic molecules, such as glucose, are structured in a spiral form: i.e. they have a definite helicity or handedness. It is this helicity which gives a molecule its ability to rotate the polarization of the incident light.

This disclosure may be better understood by restating several definitions that are known to those skilled in the art. Partial polarization means that the polarized of a particular frequency is to some degree elliptically polarized. Thus, partial polarization of polychromatic light means that each frequency in the band of light is ellictically polarized to some degree. The degree of elliptictical polarization of any one frequency depends on the conditions under which the polychromatic beam was polarized. Nevertheless, all frequencies carry some degree of elliptical polarization. Optical Rotatory Power (ORP): the polarization ellipse will rotate about an axis parallel to the direction of propagation of the light beam after traversing the sample, i.e., traversing a concentration of the target chiral molecule. Circular Dichroism (CD): the polarization ellipse will distort, or change shapeochaning its eccentricity or ellipticity after traversing the sample, i.e., a concentration of the target chiral molecule.

Detailed information on the functioning of the Photonic Molecular Probe (Photonic Molecular Probe) and its potential applications can be found in U.S. Pat. No. 5,871,442 which is incorporated by reference as if set out in full.

A desired final result in the Photonic Molecular Probe is the reliable determination of the concentration of any of a large number of species n human blood, and the determination of like concentrations of a virtually unlimited variety of biologic and non-biologic situations.

To this end the Photonic Molecular Probe makes use of certain optical, geometric, physical, chemical and electrical properties. For example, optical measurements might include, amongst others, intensities, polarization states, angles locating intensity peaks, etc. These are detected by transducers (sensors) of various types which transform such quantities into electrical signals that are more conveniently stored and processed. By a judicious selection, combination, and manipulation of these kinds of various elements, a final value of the concentration is obtained.

In the case of the Photonic Molecular Probe device, the rotation of the polarizer is incremented, stopping at predetermined angles.

$$\theta_i = \theta_1, \theta_2, \theta_3, \theta_4, \ldots, \theta_N \qquad \text{Equation 6}$$

For each $\theta_i$ a set of of intensities is generated as a function of the analyzer angle $\phi_{ji}$, $I(\phi_{ji},\theta_i) = I_{ji}$, where $1 \leq j \leq M$. For example, the following data sets, D, can be generated:

| $\theta_1$ | | $\theta_2$ | | | $\theta_N$ | |
|---|---|---|---|---|---|---|
| $\phi_{11},$ | $I(\phi_{11})$ | $\phi_{12},$ | $I(\phi_{12})$ | ... | $\phi_{1N},$ | $I(\phi_{1N})$ |
| $\phi_{21},$ | $I(\phi_{21})$ | $\phi_{22},$ | $I(\phi_{22})$ | ... | $\phi_{2N},$ | $I(\phi_{2N})$ |
| $\vdots$ | $\vdots$ | $\vdots$ | $\vdots$ | ... | $\vdots$ | $\vdots$ |
| $\phi_{M1},$ | $I(\phi_{M1})$ | $\phi_{M2},$ | $I(\phi_{M2})$ | ... | $\phi_{MN},$ | $I(\phi_{MN})$ |

Note that the subscript i on the angular variable, $\phi_{ji}$, is redundant and unnecessary. It is used to emphasize that the analyzer angle, $\phi_j$, being cited belongs to a set of intensities, $I_{ji}$, that are generated at fixed polarizer angle, $\theta_i$.

One method is to take forward differences, $\Delta I_{ji}$, amongst all the sets of $\theta_i$ values:

$$\Delta I_{ji} = I(\phi_{ji+1} + \theta_{i+1}) - I(\phi_{ji} + \theta_i) \qquad \text{Equation 7}$$

Example: j=1

$$\Delta I_{ji} = I(\phi_{ji+1} + \theta_{i+1}) - I(\phi_{ji} + \theta_i) \qquad \text{Equation 7}$$

$$\Delta I_{12} = I(\phi_{12} + \theta_2) - I(\phi_{11} + \theta_1) \qquad \text{Equation 8a}$$

$$\Delta I_{13} = I(\phi_{13} + \theta_3) - I(\phi_{12} + \theta_2) \qquad \text{Equation 8b}$$

$$\Delta I_{14} = I(\phi_{14} + \theta_4) - I(\phi_{13} + \theta_3) \qquad \text{Equation 8c}$$

$$\vdots$$

$$\Delta I_{11} = I(\phi_{11} + \theta_1) - I(\phi_{1N} + \theta_N) \qquad \text{Equation 8d}$$

Then the sets of data to be processed are:

$$j = 1\ \{\Delta I_{11}, \Delta I_{12}, \Delta I_{13}, \Delta I_{14}, \ldots, \Delta I_{1N}\} \qquad \text{Equation 9a}$$

$$\vdots$$

$$j = M\ \{\Delta I_{M1}, \Delta I_{M2}, \Delta I_{M3}, \Delta I_{M4}, \ldots, \Delta I_{MN}\} \qquad \text{Equation 9b}$$

The advantage of processing the data in this fashion is that it allows one to subtract out, to a large degree, any background signal, periodic or othewise, on which the signal information may be riding and to track the chromatic information in the partially polarized polychromatic input signal.

In the Photonic Molecular Probe model based treatment then, these doubly subscripted forward difference intensity values may be written as the sum of a model dependent component, f, and a noise, n, component:

$$\Delta I_{ji} = f_{ji}(c, \alpha) + n_{ji}, \qquad \text{Equation 10}$$

where c is the concentration of the target (measured) species, the vector parameter $\alpha$ includes all other confounding effects (such as bone, hemoglobin water, other chiral matter (proteins), etc.), and $n_{ji}$ represents the system noise. The model function many be determined from first principles if an adequate physical model of the system is already had, or phenomenologically from the system at hand. Indeed, it may also be determined by a complementary pairing of theoretical and empirical results.

Both for the above example using forward differences, and for any other data treatment version, the overall analysis is to solve or invert these equations in order to obtain c. This is most effectively done by the Bayesian method as outlined below. In this formulation the optimum amount of information, along with its associated reliability, may be extracted from each data set.

Figure 3:
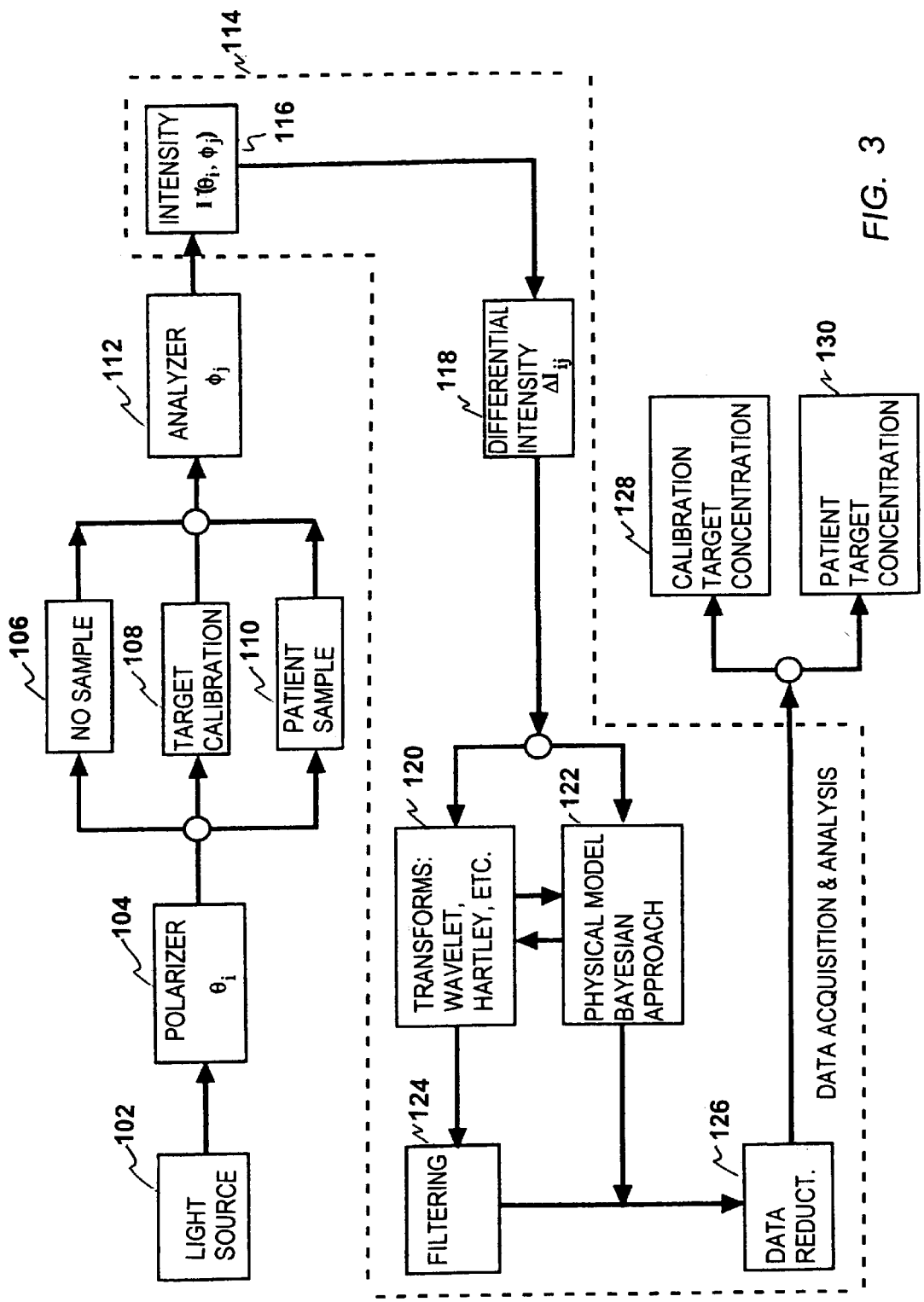

The general approach to the data acquisition and analysis, using the Photonic Molecular Probe device, is shown in flow chart form in FIG. 3. Light source 102 is optically coupled to polarizer 104. Polarizer 104 is optically coupled to an empty cell 106, a calibration target cell 108 and/or a target specimen cell 110, the optical output of which is coupled to an analyzer 112. The analyzer 112 is coupled to a data acquisition and analysis device 114 which is comprised of an intensity determination system 116, coupled to differential intensity system 118, which is coupled to a transform system 120 and a physical model 122. The Transform system 120 is coupled to a filtering system 124. The physical model 122 and the filtering system are coupled to a data reduction system 126. The Data acquisition and analysis device 114 provides a calibration the target concentration 128 and the specimen target concentration 130.

General Scheme for Frequency Selection—A Phenomenological Approach

Without the first round of data it is of course impossible to set forth a detailed frequency selection scheme: if that were possible we would not need the first round of data. However, certain guiding principles may be enumerated that will guide any specific selection of these frequencies. For illustrative purposes, glucose is cited to be the target molecule in what follows. However, the general procedure of frequency selection for any molecule of interest is the same.

1. Assume that all centered frequencies (i.e., centered within a particular narrow band width to be processed by the Photonic Molecular Probe) within the physiological window, 600 nm to 1200 nm, have equal a priori probability of being relevant/necessary/sufficient for the unique determination of glucose under all possible physiological conditions. Ideally the final signature will be exactly that—necessary and sufficient. Depending upon light sources available, or the ease/economy with which certain frequencies may be generated within this window, three or four frequencies are selected which sample the window in some approximate fashion. In other words, try to avoid all three or four frequencies being, say, below 800 nm, or from any narrow band. With this choice fixed, the instrument is then stabilized and calibrated in the usual fashion: no target, empty cuvette, distilled water, calibrated glucose solutions with and without various contaminants, in vitro blood work, and finally in vivo studies.
2. If at any of these stages of increasing complexity it is found that the introduced confounding elements (e.g. contaminants) make the chosen signature insufficient to uniquely identify glucose, then the character of the indeterminacy (degeneracy) should be examined and the nature of the optical probe is changed. This change may be the addition of more frequencies, the deletion of frequencies originally chosen, frequency shifts, etc. It may prove to be the case that the initially chosen frequencies are inadequate to determine even glucose alone in distilled water. In that case the signature modification process should begin early in the protocol so a signature unique to glucose is obtained.
3. The above process is iterated through increasingly complex environments, including any that are likely to be met in clinical practice. In this way the initial optical signal is purpose built to have the minimum complexity to completely determine glucose in any environment.

At each stage mentioned above the evaluation of the adequacy of the optical probe used is aided by the use of sophisticated data processing, enhancement, and transform techniques detailed below. Indeed, this may include a theoretical model developed for the specific system at hand.

Signal Processing and The Bayesian Method

The data acquired by the Photonic Molecular Probe contains the signature of the target molecule whose concentration needs to be determined within preset limits of accuracy. The data may contain information about other molecules that are optically active, and in general the data will be noisy. Specialized processing techniques, outlined below, are needed to delineate the presence and concentration of the molecule of interest (such as blood sugar). The choice of a particular technique depends on the range of concentrations where maximum sensitivity is desired.

In the following, the data is assumed to be a function of a sampling variable, x, such as the polarizer angle $\phi_i$, the analyzer angle $\phi_j$, the time, or any combinations of relevant sampling variables. The Photonic Molecular Probe measurement results in a discrete N dimensional data set $D=(d_1, d_2, \ldots, d_N)$ where $d_i$ is the data point at the sampling point given by $x_i$. Note that in the above example if forward differencing the data set D would be a vector valued function of a vector, $D(d_1, d_2, \ldots, d_N)$, where $d_N=\{\Delta I_{jN}\}$ for all j. If each set, $d_i$, could be reduced to a single "significant" value, by an appropriate averaging or tranformation process, then indeed, D can be represented as a simple vector, $D=(d_1, d_2, \ldots, d_N)$.

Processing Algorithms

In general, a data set is transformed into a domain in which the target signature is considerably enhanced and more easily identified than in the original domain in which the data was taken. The appropriate transform is determined by the experimental data and the precision to which the parameters being investigated is required. The power spectrum of the transformed data contains the signature of the molecule being probed. With in the power spectrum the position of various peaks and their widths collectively contain this information.

It must be emphasized that the power spectrum is used for purposes of illustration and example. The data transformations certainly are not limited to this particular transform. The value of a transform lies in its utility, and depending on the particular experiment (target, instrument version, target matrix, etc.) the transform of greatest utility is chosen from the universe of possible transforms. This is clearly implied in the flow chart of FIG. 3. In fact, a combination of several transforms maybe needed for various regions of optical frequency response.

With one embodiment of the Photonic Molecular Probe, a measurement is first done without any sample present. The measurement is repeated several times over in order to obtain a statistically good sample space that is needed to characterize the noise spectrum and the background. Next, data sets are generated by making in vitro measurements on specially prepared samples containing known concentrations of the target molecule under study. The area of the power spectrum in a given frequency window is then calibrated against the concentration. Comparison of the power spectrum with the background power spectrum enables one to set up thresholds of delectability for various concentration of the target molecule. From the background power spectrum, as well as the power spectra of the known controlled samples, receiver operating characteristic (ROC) curves that give the probability of detection versus probability of false alarm are constructed. An estimate of the confidence level in the determined concentration is obtained directly from the ROC curve. This is done for numerous concentrations in order to build a reference sample library. With the use of this library, an estimate of the concentration of the target molecule in an unknown sample may be obtained from its power spectrum.

The choice of a particular transform domain (frequency, wavelet, etc.) is a decision that is made on a empirical basis and will more than likely depend on the target molecule and the desired level of concentration sought after. Clearly, the simplest and easiest place to start the process is with the standard Fast Fourier Transform—the FFT.

Model Based Algorithms

In this method, the data D is expressed in terms of a physical model function f as $$d_\beta = f\beta(c, \alpha) + n_{62}.\qquad\text{Equation 11}$$

Where the subscript $\beta$ stands for collection of all possible relevant indicies needed to define the model function—with reference to Eq.(5) $\beta$=ji. The model function can be either specified empirically or from a first principles study of the interaction of light with the system under consideration. The quantity c is the concentration of the molecule of interest. The set of parameters, $\alpha$, include quantities such as the concentration of other molecules, the optical response frequencies, or any other quantity that may be encounted in the measurement process. The model function itself can be expanded in terms of a set of basis functions G, $$f_\beta(c, \alpha) = \sum_k B_k G_{k\beta}(c, \alpha),\qquad\text{Equation 12}$$

where the $\{B_k\}$ are the associated expansion coefficients. The choice of the model functions is unique to the Photonic Molecular Probe device and the nature of target system to be investigated.

Nonlinear Least Squares Algorithm

In this approach a mean square error is defined as $$E = \sum_\beta w_\beta(d_\beta - f_\beta(c, \alpha))^2.\qquad\text{Equation 13}$$

Here $w_\beta$ is the weight associated with the data point $d_i$ and can typically be chosen to be $1/\sigma_\beta^2$, where $\sigma_\beta$ are the uncertainties, characteristic of the noise, in the ith data point. The parameter set $\{c,\alpha\}$ is then determined by the minimization of E in the parameter space by a variation of all the unknown parameters in the model function as well the choice of its functional form. The algorithm for minimization of E can be any one of the standard minimization algorithms. For example, that of Marquardt's which combines the best features of the gradient search method with the method of linearizing the fitting (model) function.

The estimates obtained by this algorithm are biassed by the values of the other unknown parameters. The technique may not work very well for detection of low concentrations of the target molecule, for example, concentrations <100 mg/ltr of blood glucose. The Bayesian algorithm, discussed below, does not have this problem.

Bayesian Algorithm

In this method the determination of the probability density for the concentration c of the target molecule is conditioned on the data, D, and any prior information, I. The method is an outgrowth of Bayes' theorem on conditional probabilities.

The probability density for all the parameters c, $\alpha$ conditioned on data D can be written using Bayes' theorem as $$P(c\alpha \mid DI) = \frac{P(D \mid c\alpha I)P(c\alpha \mid I)}{P(D \mid I)},\qquad\text{Equation 14}$$

where $P(D|c\ \alpha I)$=Likelihood Function,    Equation 15a $P(c\ \alpha|I)$=Prior Probability Density,    Equation 15b $P(D|I)$=Probability Density for D.    Equation 15c When the noise in the data is Gaussian, the likelihood function is Gaussian and is given by $$P(D \mid c\alpha I) = \prod_{i=1}^N \frac{1}{(2\pi\sigma_\beta^2)^{1/2}} \exp(-(d_\beta - f_\beta(c, \alpha))^2/2\sigma_\beta).\qquad\text{Equation 16}$$

Once the prior information is specified the probability density for c,$\alpha$ can be obtained. (Note that under certain circumstances some data points might be measured with better or worse precision than others. This can quantitatively be accounted for by assigning a different "parent" distribution—a distribution containing an infinite number of measurements from which the true probability of getting a particular observation in one measurement may be obtained—to those data points with the same mean but with a correspondingly smaller or larger standard deviation, $\sigma_i$. It is assumed that this is not the case and thus there is only one parent distribution and all $\sigma_i$'s are the same and equal to $\sigma$.) The probability density of interest, $P_R(c|I)$, can then be estimated from $$P_R(c|I) = \int d\alpha P(c\alpha|D\ I)\qquad\text{Equation 17}$$

The integral averages over, in effect integrates out, all the parameters that are not of interest. This removes any statistical bias these parameters may have in the estimate of the concentration distribution. The most probable concentration, c*, is then determined from the maximum of this probability density as a function of c and the associated variance on this estimate can be obtained from the width of this probability density—that is by taking the distribution's second moment about c*.

In general, the generic problem of locating and identifying a macroscopic target, to a high degree of certainty, within a noisy, cluttered background, with possible distortions of the target, has been done via ad hoc procedures and the use of matched or correlation filters. However, it has been recently argued in the literature that correlation methods should be supported by a sound theoretical foundation derived from well-established methods of signal processing which include accurate parameter estimation. One approach to parameter estimation is from the Bayesian standpoint, according to which prior knowledge regarding the parameters to be estimated, or regarding the problem in general, can be taken into account using Bayes' Theorem.

While still relatively new and not widely used the results of Bayesian statistics applied to pattern recognition problems have been very encouraging. In the worst case scenario the Bayesian approach produces results of parameter estimation which are as good as those obtained by using correlation methods. In general, however, the results are much better. The application of this method to the areas of physiological systems and medical diagnostics, such as the assay of blood constituents, as well as concentration levels, has not been done before.

Concentration Data Base

In order to achieve the maximum likelihood of identifying and a quantifying the target molecule under various conditions a multi-dimensional data-base will be generated using the Photonic Molecular Probe device. The database will store information on the concentration of the targeted molecule as a function of time and other salient features such as race, sex, etc.

Neural Network Processing

A neural network architecture will be trained on standard concentration patterns according to individuals, including race, sex, etc. This neural network will then be used to correlate a new sample data against existing library of patterns.

PMP Signal Processor Chip

All the algorithms described above will be implemented on a digital signal processing integrated circuit or an Application Specific Integrated Circuit (ASIC) that resides within the housing of the Photonic Molecular Probe device. The data acquisition and analysis device 114 of FIG. 3 can be programmed onto the chip.

Single chip digital processors, such as microcontrollers, microprocessors, or digital signal processors, are ubiquitous digital computers used in virtually every application where intelligent control, information processing, or real-time signal processing is important. The tasks a digital processor can efficiently fulfill are directly related to the internal organization, or architecture, of the processor. The more generalized the task(s), the more general the architecture. For example, the architecture of microprocessors, such as those used in personal computers, is more geared toward general information handling, compared to a microcontroller for a milling machine. Digital signal processors, or DSPs, are specialized digital computers. Unlike microprocessors, DSPs are adapted for efficient, often repetitive, processing of data. For example, a DSP may be used for filtering, detecting, and generating digitized analog signals in a modem. DSPs may also be used for processing signaling information from individual telephone lines and trunks in an electronic switching system. In either case, the task assigned to the DSP is specialized and repetitive—the faster the DSP can perform the assigned task, the greater the signal bandwidth that can be processed or the more telephone line signaling information that can be processed by one processor.

The architecture of a typical microprocessor has general purpose registers and arithmetic circuits arranged to process widely different tasks, such as text editing, spreadsheets, etc. As a consequence, the execution of those tasks are done not as quickly, or as efficiently, as a processor tailored for optimal performance of a particular task. A DSP, on the other hand, has specialized registers and arithmetic circuits for efficient processing of signals. For example, multiply-and-accumulate instructions are very common operations in signal processing algorithms and are usually implemented only in DSPs, not on microprocessors.

In view of the foregoing description, numerous modifications and alternative embodiments of the invention will be apparent to those skilled in the art. Accordingly, this description is to be construed as illustrative only and is for the purpose of teaching those skilled in the art the best mode of carrying out the invention. Details of the structure may be varied substantially without departing from the spirit of the invention, and the exclusive use of all modifications which come within the scope of the appended claim is reserved.

We claim:

1. In an opto-electronic device utilizing a band of light for quantitative analysis of a specimen containing a target molecule, the opto-electronic device comprising a specimen cell adapted for receiving the specimen and for transporting the band of light, a device for comparing the band of light before entering the specimen with the band of light after exiting the specimen, the device for comparing comprising:

an optical sensor; and, a signal processor for determining a quantitative level of the target molecule within the specimen;

wherein the signal processor utilizes Bayes's Theorem for determining the quantitative level of the target molecule within the specimen and a probability density of interest is estimated as $P_R(c|I)$, is estimated as $P_R(c|I) = \int d\alpha P(c\alpha|DI)$, where c is the concentration of the target molecule conditioned on data D and any prior information I, and the probability density for parameters c, $\alpha$ conditioned on data D is $$P(c\alpha | DI) = \frac{P(D | c\alpha I)P(c\alpha | I)}{P(D | I)},$$

where $P(D|c\alpha I)$=Likelihood Function,
$P(c\alpha|I)$=Prior Probability Density,
$P(D|I)$=Probability Density for D.

2. The opto-electronic device as recited in claim 1 wherein the target molecule changes ellipticity of said segmented characterized light.

3. In an opto-electronic device utilizing a band of partially polarized polychromatic light for quantitative analysis of a specimen containing a target molecule, the opto-electronic device comprising a specimen cell adapted for receiving the specimen and for transporting the band of partially polarized polychromatic light, a device for comparing the band of partially polarized polychromatic light before entering the specimen with the band of partially polarized polychromatic light after exiting the specimen, the device for comparing comprising:

an optical sensor; and, a signal processor for determining a quantitative level of the target molecule within the specimen;

wherein the signal processor utilizes Bayes's Theorem for determining the quantitative level of the target molecule within the specimen and a probability density of interest is estimated as $P_R(c|I)$, is estimated as $P_R(c|I)=\int d\alpha P(c\alpha|DI)$, where c is the concentration of the target molecule conditioned on data D and any prior information I, and the probability density for parameters c, $\alpha$ conditioned on data D is $$P(c\alpha|DI) = \frac{P(D|c\alpha I)P(c\alpha|I)}{P(D|I)},$$

where
  $P(D|c\alpha I)$=Likelihood Function,
  $P(c\alpha|I)$=Prior Probability Density,
  $P(D|I)$=Probability Density for D.

4. A method for quantitative analysis of a target molecule within a specimen, said method comprising the steps of:
  producing elliptical/partially polarized polychromatic light;
  producing segmented characterized light with a polarizer optically coupled to said elliptical/partially polarized polychromatic light;
  transporting said segmented characterized light onto and through the specimen;
  polarizing said segmented characterized light exiting the specimen; and
  comparing said segmented characterized light before entering the specimen with said segmented characterized light after exiting the specimen by utilizing Bayes' Theorem for determining the quantitative level of the target molecule within the specimen;
  estimating a probability density of interest as $P_R(c|I)$, is estimated as $P_R(c|I)=\int d\alpha P(c\alpha|DI)$, where c is the concentration of the target molecule conditioned on data D and any prior information I, and the probability density for parameters c, $\alpha$ conditioned on data D is $$P(c\alpha|DI) = \frac{P(D|c\alpha I)P(c\alpha|I)}{P(D|I)},$$

where
  $P(D|c\alpha I)$=Likelihood Function,
  $P(c\alpha|I)$=Prior Probability Density,
  $P(D|I)$=Probability Density for D.

5. The method as recited in claim 4 further comprising the step of coupling an RF source to the specimen whereby said RF source causes particular changes of selected achiral molecules within the specimen.

6. The method as recited in claim 4 wherein the target molecule changes ellipticity of said segmented characterized light.

* * * * *